United States Patent [19]

Kreft, III et al.

[11] Patent Number: 5,250,693
[45] Date of Patent: * Oct. 5, 1993

[54] QUINOLINYLMETHOXY NAPHTHALENEPROPIONIC ACID DERIVATIVES AS ANTI-INFLAMMATORY/ANTIALLERGIC AGENTS

[75] Inventors: Anthony F. Kreft, III, Langhorne, Pa.; John H. Musser, Alameda, Calif.; James J. Bicksler, Cranbury, N.J.; John W. Giberson, Newtown; Dennis M. Kubrak, Fairless Hills, both of Pa.; Annette L. Banker, Plainsboro, N.J.

[73] Assignee: American Home Products Corporation, New York, N.Y.

[*] Notice: The portion of the term of this patent subsequent to Jan. 28, 2009 has been disclaimed.

[21] Appl. No.: 806,518

[22] Filed: Dec. 13, 1991

Related U.S. Application Data

[63] Continuation-in-part of Ser. No. 578,367, Sep. 6, 1990, Pat. No. 5,084,575, which is a continuation-in-part of Ser. No. 351,119, May 12, 1989, Pat. No. 4,960,892, which is a continuation-in-part of Ser. No. 202,975, Jun. 10, 1988, abandoned, which is a continuation-in-part of Ser. No. 80,122, Jul. 31, 1987, abandoned.

[51] Int. Cl.$^5$ .......................... C07D 215/38
[52] U.S. Cl. .................... 546/175; 546/174
[58] Field of Search ............... 546/152, 172, 174, 175

[56] References Cited

U.S. PATENT DOCUMENTS 5,084,575  1/1992  Kreft, III et al. ............. 546/172

Primary Examiner—Thurman K. Page
Assistant Examiner—Jyothsna Vankat
Attorney, Agent, or Firm—George Tarnowski

[57] ABSTRACT

There are disclosed compounds of the formula

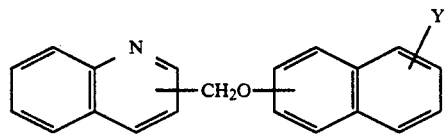

wherein
R is hydrogen or lower alkyl;
Y is

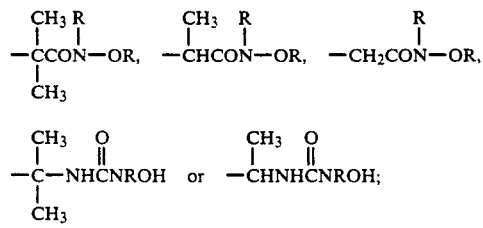

or a pharmaceutically acceptable salt thereof, and its use in the treatment of leukotriene-mediated nasobronchial obstructive airpassageway conditions, such as allergic rhinitis, allergic bronchial asthma and the like, in psoriasis, ulcerative colitis, rheumatoid arthritis as well as in other immediate hypersensitivity reactions.

6 Claims, No Drawings

QUINOLINYLMETHOXY NAPHTHALENEPROPIONIC ACID DERIVATIVES AS ANTI-INFLAMMATORY/ANTIALLERGIC AGENTS

This is a continuation-in-part of U.S. patent application Ser. No. 578.367, filed Sep. 6, 1990 and now U.S. Pat. No. 5,084,575, issued Jan. 28, 1992, which is a continuation-in-part of U.S. patent application Ser. No. 351,119, filed May 12, 1989, and now U.S. Pat. No. 4,960,892, issued Oct. 2, 1990, which is a continuation-in-part of U.S. patent application Ser. No. 202,975, filed Jun. 10, 1988, now abandoned, which is a continuation-in-part of U.S. patent application Ser. No. 080,122, filed Jul. 31, 1987, now abandoned.

This invention relates to novel naphthalenepropionic acid derivatives possessing lipoxygenase inhibitory and leukotriene antagonist activity, which are useful as and-inflammatory, antiallergic and cytoprotective agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.*, 215, 115–118 (1980); *Biochem, Biolphys, Res, Commun.*, 93, 1121–1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that LTC4 and $LTD_4$ are potent bronchoconstrictors of the human bronchi [see Dahlen et al., *Nature* 288, 484–486 (1980) and Piper, *Int, Arch, Appl, Immunol.*, 71, suppl. 1, 41 (1985)] which stimulate the release of mucus from airways in vitro [Marom et al., *Am. Rev, Resp. Dis.*, 126, 449 (1982)], are potent vasodilators in skin [see Bisgaard et al., *Prostaglandins*, 22, 797 (1982)], and produce a wheal and flare response [Camp et al., *Br. J. Pharmacol.*, 80, 497 (1983)]. The nonpeptide leukotriene, $LTB_4$, is a powerful chemotactic factor for leukocytes [see A. S. Ford-Hutchinson, *J. Roy, Soc, Med.*, 74, 831-833 (1981)], which stimulates cell accumulation and affects vascular smooth muscle [see Bray, *Br. Med, Bull.*, 39, 249 (1983)]. The activity of leukotrienes as mediators of inflammation and hypersensitivity is extensively reviewed in Bailey and Casey, *Ann. Reports Med. Chem.*, 1-7, 203–217 (1982) and in Bray, *Agents and Actions*, 19, 87 (1986).

There is also evidence that products of the cyclooxygenase/lipoxygenase pathways play key roles in both the pathogenesis of gastric mucosal damage due to extracellular (gastric and intestinal contents, microorganisms, and the like) or intracellular (ischemia, viruses, etc.) agents, as well as in cytoprotection against such damage. Thus, on the one hand prostaglandins exert a cytoprotective effect on the gastric mucosa [see Robert, *Gastroenterology*, 77, 761–767 (1979)]and this action of the prostaglandins, especially of the E series, is considered to be of importance in the treatment of gastrointestinal ulceration [see Isselbacher, *Drugs*, 33 (suppl.), 38–46 (198)]. On the other hand, ex vivo experiments have shown that gastric mucosal tissue from ethanol-pretreated rats is capable of $LTC_4$ generation and that this $LTC_4$ production is quantitatively related to the severity of the ethanol damage [see Lange et al., *Naunyn-Schmiedeberg's Arch. Pharmacol. Suppl.*, 330, R27, (1985)]. It has also been demonstrated that $LTC_4$ can induce vasoconstriction in both venous and arterioler vessels in the rat submucosa [see Whittle, *IUPHAR Ninth Int. Cong. of Pharm.*, S30-2, London, England (1984)]. This is significant since ethanol-induced lesion formation in gastric mucosa may be multifactorial with, for example, stasis of gastiic blood flow contributing significantly to the development of the hemoffhagic necrotic aspects of the tissue injury [see Guth et al., *Gastroenterology*, 87, 1083–90 (1984)]. Moreover, in the anesthetized cat, exogenous $LTD_4$ evokes both increased pepsin secretion and decreased transgastric potential [Pendleton et all, *Eur. J. Pharmacol.*, 125, 297–99 (1986)]. A particularly significant recent finding in this regard is that 5-lipoxygenase inhibitors and some leukotriene antagonists protect the gastric mucosa against lesions induced by the oral or parenteral administration of most nonsteroidal antiinflammatory drugs [see Rainsford, *Agents and Actions*, 21, 316–19 (1987)]. Accordingly, a significant body of evidence implicates the involvement of lipoxygenase products in the development of pathological features associated with gastric mucosal lesions, such as for example those induced by ethanol exposure and administration of non-steroidal anti-inflammatory drugs. Thus, compounds which inhibit the biological effects of leukotrienes and/or which control the biosynthesis of these substances, as by inhibiting 5-lipoxygenase, are considered to be of value as cytoprotective agents.

Accordingly, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation and for gastric cytoprotection must focus on either blocking the release of mediators of these conditions or antagonizing their effects. Thus compounds, which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions and in providing gastric cytoprotection.

It has now been found that certain novel naphthalenepropionic acid derivatives inhibit lipoxygenase and antagonize products of the hpoxygenase pathway, and so are useful as anti-inflammatory, anti-allergic and cytoprotective agents. The present invention provides novel compounds having the following formula:

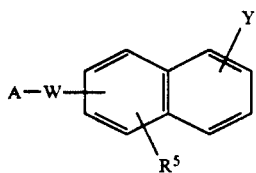

wherein

A is alkyl of 3-19 carbon atoms, diloweralkyl allyl, dihaloallyl, diphenylallyl, lower alkynyl,

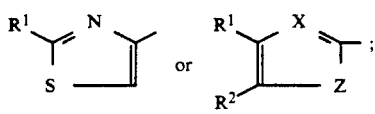

W is —CR₂O—, —CH=CH— or —CH=CHCH₂O—
X is N or CR;
Z is

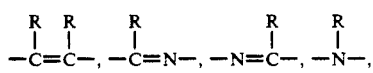

—S— or —O—;
R is hydrogen or lower alkyl;
Y is —COR³,

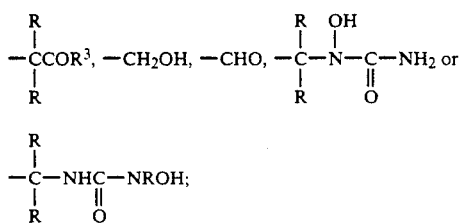

R¹ is hydrogen, lower alkyl or phenyl;
R² is hydrogen or lower alkyl; or
R¹ and R² taken together form a benzene ring, optionally substituted by halo;
R³ is —OR ,

or —NHSO₂R⁴;
R⁴ is phenyl or loweralkyl substituted phenyl;
R⁵ is halo;
and the pharmaceutically acceptable salts thereof.

The terms "lower alkyl" and "lower alkynyl" refer to moieties having 1 to 6 carbon atoms in the carbon chain, and "halo" refers to fluoro, chloro or bromo.

The compounds of the invention can be readily prepared according to the following representative reaction sequence:

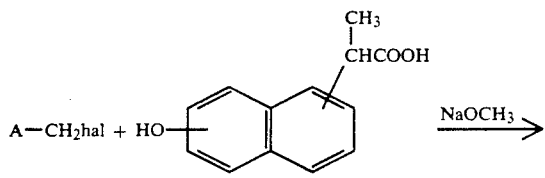

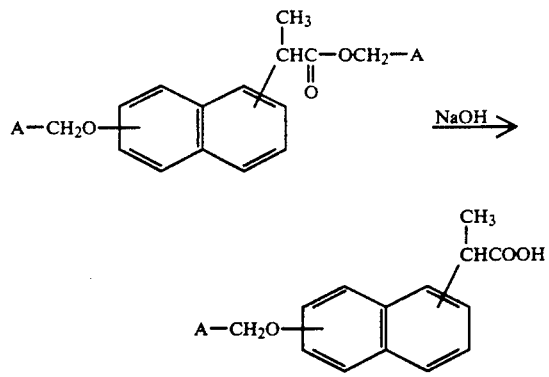

In the above reaction sequence, A is as defined hereinbefore and hal denotes chloro, bromo or iodo. This preparative sequence reacts two equivalents of the starting material ACH₂hal with a metal derivative of the hydroxynaphthalene propionic acid to form an intermediate ester ether which is hydrolyzed to yield the desired final products. The metal derivative of the hydroxynaphthalene propionic acid may be prepared by treating the acid with an alkali metal alkoxide, such as sodium methoxide. In an alternative sequence, it is possible to use only one equivalent of starting material ACH₂hal with the metal derivative to obtain the desired final product directly, without proceeding through the ethyl ester intermediate.

In another reaction sequence, for example, the desired final products can be prepared by the alkylation of alkyl esters of hydroxynaphthalene propionic acid:

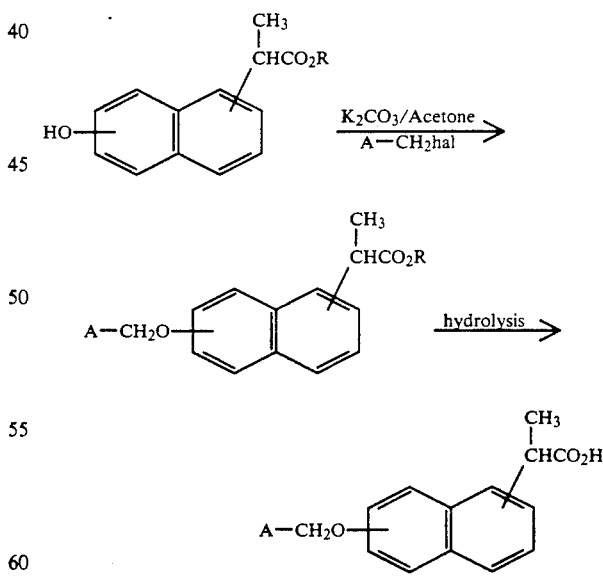

where hal is as defined hereinbefore and R is lower alkyl. Hydrolysis is carried out using a dilute hydroxide, such as for example sodium hydroxide.

Compounds of the invention having other Y substituents can be prepared according to the following reaction schemes:

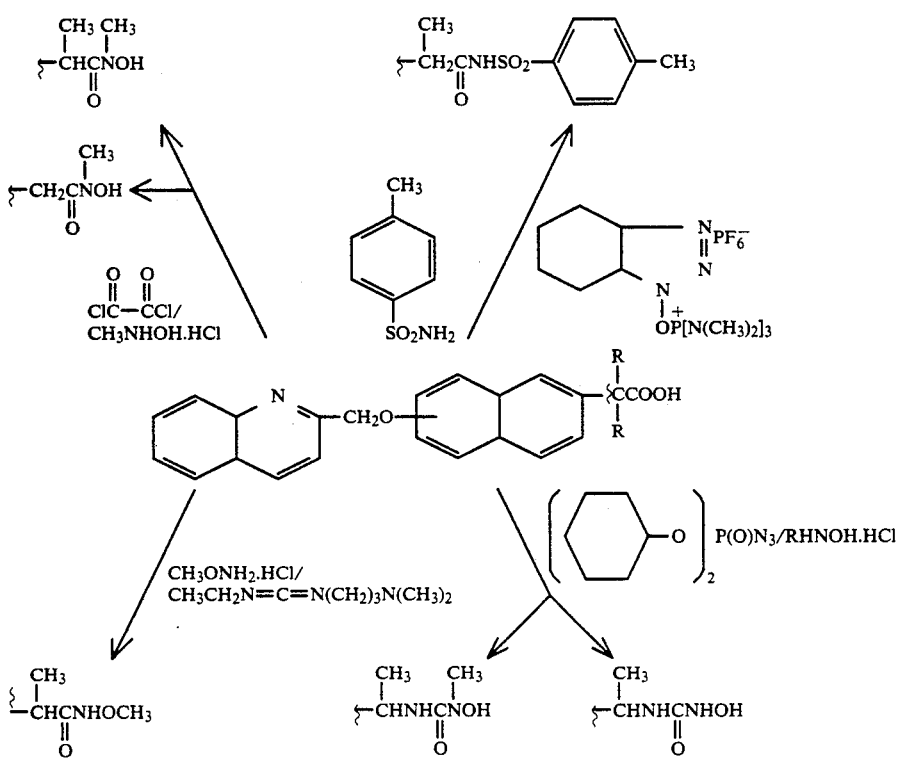

The starting materials used in the reaction sequences are available commercially or can be prepared by known methods conventional in the art. Thus, for example, the benzo-fused heterocyclic compounds such as 1-methyl-2-chloromethylbenzimidazole, 2-chloromethylbenzthiazole and 2-chloromethylbenzoxazole can be prepared by the following reaction scheme:

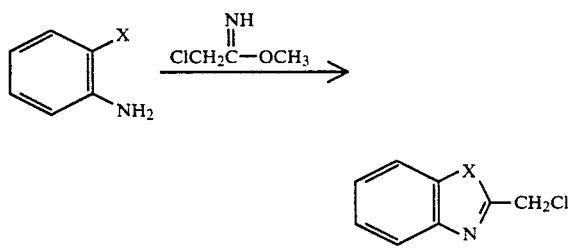

wherein X is O, S or NCH$_3$. The reaction is preferably carried out at a controlled low temperature in an organic solvent, such as methylene chloride.

The compounds of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic. The compounds which are carboxylic acids are capable of forming alkali metal and alkaline earth carboxylates and carboxylates of pharmacologically acceptable cations derived from ammonia or a basic antine. Examples of the latter include but are not limited to cations such as ammonium, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium 1-isopropylpyrrolidinium, 1,4-dimethylpiperazinium, 1-n-butyl-piperidinium, 2-methylpiperidinium, I-ethyl-2-methylpiperidinium, mono-, di- and triethanolammonium, ethyl diethanolammonium, n-butylmonoethanolammonium, tris(hydroxymethyl)methylammonium, phenylmonoethanolarnmonium, and the like.

The compounds of the invention, by virtue of their ability to inhibit the activity of lipoxygenase enzyme and to antagonize mediators arising from this enzymatic pathway, are useful in the treatment of inflammatory conditions. Accordingly, the compounds are indicated in the treatment of such diseases as rheumatoid arthritis, osteoarthritis, tendinitis, bursitis and similar conditions involving inflammation. Moreover, by virtue of their ability to inhibit the activity of lipoxygenase enzyme and by their ability to antagonize the effect of LTC$_4$, LTD$_4$ and LTE$_4$ which are the constituents of SRS-A, they are useful for the inhibition of symptoms induced by these leukotrienes. Accordingly, the compounds are indicated in the prevention and treatment of those disease states in which LTC$_4$, LTD$_4$ and LTE$_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

The compounds of the invention are cytoprotective agents and are considered especially useful when administered with conventional non-steroidal anti-inflammatory drugs, whose major side effect is gastrointestinal irritation. The cytoprotective effect of the compounds of the invention significantly reduces the gastroirritant impact of conventional anti-inflammatory drugs. Ibis effect is based not only on the ability of the compounds of the invention to inhibit the biological effects of leukotrienes and/or control the biosynthesis of these substances, as by inhibiting lipoxygenase, but also by a shunting effect, whereby the control of the lipoxygenase pathway "shunts" the oxidation of arachidonic acid into the cyclooxygenase pathway, giving rise to an increase in the formation of cytoprotective prostaglandins. These biological effects make the compounds of the invention especially useful in treating such conditions as erosive esophagitis, inflammatory bowel disease and induced hemorrhagic lesions such as those induced by alcohol or non-steroidal anti-inflammatory drugs (NSAID's), hepatic ischemia, noxious agent induced damage or necrosis of hepatic, pancreatic, renal or myocardial tissue; liver parenchymal damage caused by hepatotoxic agents such as carbon tetrachloride and D-galactosamine; ischemic renal failure; disease-induced hepatic damage; bile salt-induced pancreatic or gastric damage; trauma or stress-induced cell damage; and glycerol-induced renal failure.

When the compounds of the invention are employed in the treatment of allergic airway disorders, as anti-inflammatory agents and/or as cytoprotective agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects as well as the antiinflammatory and cytoprotective effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE; the in vivo ability of the compounds to inhibit bronchospasm induced by exogenously administered mediators of bronchoconstriction; measure the in vivo activity of the compounds as antiinflammatory agents in the rat carrageenan paw edema and reverse passive Arthus assays; measure the potential of the compounds to induce acute gastroirritation in rats; measure the ability of the compounds to prevent acute gastroirritation in rats induced by non-steroidal anti-inflammatory drugs.

The following examples show the preparation and pharmacological testing of compounds within the invention.

EXAMPLE 1

α-Methyl-6-(2-quinolinylmethoxy)-2-naphthaleneacetic acid

To a solution of 6-hydroxy-(α-methyl-2-naphthaleneacetic acid (10.8 g, 50 mmol) in methanol (100 ml) is added sodium methoxide (100 mmol). After 10 minutes the solvent is removed and replaced with dimethylformamide (250 ml). 2-(Chloromethyl)quinoline (17.8 g, 100 mmol) is then added and the reaction mixture is stirred for 8 days at room temperature. The reaction mixture is partitioned between water and methylene chloride, the organic layer is washed with water and evaporated to yield 27 g of an oil. Recrystallization of this oil twice from acetonitrile gives 10.6 g of white crystals of intermediate ether ester (42% yield, m.p. 106°-108° C.).

The ether ester from above is hydrolyzed as follows: a solution of the ether ester (14.4 g, 28.9 mmol) in a mixture of 110 ml of 1N NAOH and 110 ml tetrahydrofuran is refluxed for 1 hour. The organic solvent is then removed and 2-(hydroxymethyl)quinoline is filtered off. The aqueous solution is acidified to pH 6 and the precipitate is filtered and recrystallized from ethanol to afford 2.2 g of white crystals (21% yield, m.p. 186°-187° C.).

Analysis for: $C_{23}H_{19}NO_3$
Calculated: C, 77.30; H, 5.36; N, 3.92.
Found: C, 77.69; H, 5.36; N, 3.93.

EXAMPLE 2

α-Methyl-6-(phenylmethoxy)-2-naphthaleneacetic acid

To a solution of 6-hydroxy-α-methyl-2-naphthaleneacetic acid (6.48 g, 30 mmol) in methanol (100 ml) is added sodium methoxide (60 mm). After 10 minutes the solvent is removed and replaced with dimethylformamide (100 ml). Benzyl chloride (7.6 g, 60 mmol) is then added and the reaction mixture is stirred overnight at room temperature. The reaction is then heated at 150° C. for 1 hour. The solvent is then removed and the residue is partitioned between water and methylene chloride. The organic layer is washed with water, dried over magnesium sulfate and evaporated to 11.5 g of crude product. This crude product is extracted with 100 ml hot hexane which affords 3.5 g of white crystals. A final recrystallization from methanol affords 2.5 g of white crystals of the intermediate ethyl ester (21 % yield, m.p. 76°-78° C.).

The ether ester (2.2 g, 5.56 mmol) is hydrolyzed using the method of Example 1. Recrystallization from ethanol affords 1.1 g of white crystals (65% yield, m.p. 149°–151° C.).

Analysis for: $C_{20}H_{18}O_3$
Calculated: C, 78.40; H, 5.92.
Found: C, 7 8.3 1; H, 6.02.

EXAMPLE 3

(α-Methyl-6-[(1-methyl-1H-benzimidazol-2-yl)-methoxy]-2-naphthaleneacetic acid

The procedure of Example 2 is followed on a 10 mmol scale, substituting 2-chloromethyl-N-methyl-benzimidazole for benzyl chloride. Normal workup affords 2.5 g of white crystals of ether ester (50% yield, m.p. 228–230° C). This material is analytically pure and needs no recrystallization.

The ether ester (2.5 g, 4.9 mmol) is hydrolyzed according to the method of Example 1. Recrystallization from ethanol affords 0.75 g of white crystals (43% yield, m.p. 216–219° C.).

Analysis for: $C_{22}H_{20}N_2O_3 \cdot 3/4\ H_2O$
Calculated: C, 70.66; H, 5.79; N, 7.49.
Found: C, 70.89; H, 5.72; N, 7.28.

EXAMPLE 4

α-Methyl-6-(2-pyridinylmethoxy)-2-naphthaleneacetic acid

To a solution of 6-hydroxy-(α-methyl-2-naphthaleneacetic acid (10.8 g, 50 mmol) in methanol (100 ml) is added sodium methoxide (100 mmol). After 10 minutes the solvent is removed and replaced with hexamethylphosphoric triamide (250 ml). 2-(Chloromethyl)pyridine (100 mmol) is then added and the reaction is stirred for 5 days. The reaction is worked up by partitioning between water and methylene chloride, and the organic extract is evaporated to a crude oil which is chromatographed on silica gel (eluant:methylene chloride - ethyl acetate) to afford 6.0 g of ether ester as an oil.

The ether ester is hydrolyzed using the method of Example 1. Recrystallization from ethanol affords 5.5 g of white crystals (36% yield, m.p. 185°–187° C.).

Analysis for: $C_{19}H_{17}NO_3$
Calculated: C, 74.24; H, 5.57; N, 4.56.
Found: C, 74.49; H, 5.63; N, 4.49.

EXAMPLE 5

α-Methyl-6-(2-benzothiazolylmethoxy)-2-naphthaleneacetic acid

The title compound is prepared according to the method of Example 1, using 2-(chloromethyl)benzothiazole. White crystals are obtained having a melting point of 169°–171° C.

Analysis for: $C_{21}H_{17}NO_3S \cdot 1/4\ H_2O$
Calculated: C, 68.55; H, 4.79; N, 3.80.
Found: C, 68.44; H, 4.89; N, 4.21.

EXAMPLE 6

α-Methyl-6-(2-naphthalenylmethoxy)-2-naphthaleneacetic acid

The title compound is prepared according to the method of Example 1 using 2-(chloromethyl)naphthalene. White crystals are obtained having a melting point of 216°–218° C.

Analysis for: $C_{24}H_{20}O_3$
Calculated: C, 80.88; H, 5.66.
Found: C, 80.68; H, 5.89.

EXAMPLE 7

S-(+)-α-Methyl-6-(2-quinolinylmethoxy)-2-naphthaleneacetic acid

To a solution of S-(+)-α-methyl-6-hydroxy-2-naphthaleneacetic acid* (21.6 g, 100 mmol) in methanol (250 ml) is added sodium methoxide (200 mmol). The solvent is removed in vacuo and replaced with dimethylformamide (300 ,l). To this solution is added 2-(chloromethyl)quinoline (17.7 g, 100 mmol). After 90 minutes, the solvent is removed in vacuo at 50° C. and the residue is partitioned between ethyl acetate and pH=4 buffer. The insolubles and the ethyl acetate are heated to 60° C. at which point a homogeneous solution is obtained. Cooling the solution to room temperature affords 8.9 g of white crystals (26%). A second recrystallization of 4.0 g of this material from methanol (200 ml) affords 1.78 g of white crystals, m.p. 192–194° C.

*Prepared according to the procedure described in *J. Med. Chem.*, 17, 377 (1974).

Analysis for: $C_{23}H_{19}NO_3$
Calculated: C, 77.30; H, 5.36; N, 3.92.
Found: C, 76.96; H, 5.44; N, 3.89.
$(\alpha)_D = +51.7$ (Pyr c=1.115)

EXAMPLE 8

R-(−)-α-Methyl-6-(2-quinolinylmethoxy)-2-naphthaleneacetic acid

The title compound can be prepared according to the method of Example 7, using R-(−)-α-methyl-6-hydroxy-2-naphthaleneacetic acid. White crystals are obtained having a melting point of 190°–193° C.

Analysis for: $C_{23}H_{19}NO_3$
Calculated: C, 77.30; H, 5.36; N, 3.92.
Found: C, 76.87; H, 5.54; N, 3.77.
$(\alpha)_D = -52.96$ (Pyr c=1.08)

EXAMPLE 9

α-Methyl-6-1(2-phenyl-4-thiazol)methoxyl-2-naphthaleneacetic acid

The title compound is prepared according to the method of Example 7 using 2-phenyl-4-(chloromethyl)-thiazole and racemic 6-hydroxy-(X-methyl-2-naphthaleneacetic acid. White crystals are obtained having a melting point of 163°–164° C.

Analysis for: $C_{23}H_{19}NO_3S$
Calculated: C, 70.93; H, 4.92; N, 3.60.
Found: C, 70.75; H, 4.77; N, 3.32.

EXAMPLE 10

α-Methyl-6-(hexyloxy)-2-naphthaleneacetic acid

The title compound is prepared according to the method of Example 7 using 1-iodohexane and racemic 6-hydroxy-α-methyl-2-naphthaleneacetic acid. White crystals are obtained having a melting point of 88°–9 1° C.

Analysis for: $C_{19}H_{24}O_3$
Calculated: C, 75.97; H, 8.05.
Found: C, 76.20; H, 8.25.

EXAMPLE 11

α-Methyl-6-(butyloxy)-2-naphthaleneacetic acid

The title compound is prepared according to the method of Example 7 using 1-iodobutane and racemic 6-hydroxy-(α-methyl-2-naphthaleneacetic acid. White crystals are obtained having a melting point of 125°-127° C.

Analysis for: $C_{17}H_{20}O_3$
Calculated: C, 74.97; H, 7.40.
Found: C, 75.04; H, 7.02.

EXAMPLE 12

α-Methyl-6-(pentiloxy)-2-naphthaleneacetic acid

The title compound is prepared according to the method of Example 7 using 1-iodopentane and racemic 6-hydroxy-a-methyl-2-naphthaleneacetic acid. White crystals are obtained having a melting point of 97°-99° C.

Analysis for: $C_{18}H_{22}O_3$
Calculated: C, 75.50; H, 7.74.
Found: C, 75.54; H, 7.68.

EXAMPLE 13

α-Methyl-6-(dodecyloxy)-2-naphthaleneacetic acid

The title compound is prepared according to the method of Example 7 using 1-iodododecane and racemic 6-hydroxy-(α-methyl-2-naphthaleneacetic acid. White crystals are obtained having a melting point of 96°-97° C.

Analysis for: $C_{25}H_{36}O_3$
Calculated: C, 78.08; H, 9.44.
Found: C, 78.10; H, 9.77.

EXAMPLE 14

α-Methyl-6-(3-methyl-2-butenoxy)-2-naphthaleneacetic acid

The title compound is prepared according to the method of Example 7 using 1-bromo-3-methyl-2-butene and racemic 6-hydroxy-(α-methyl-2-naphthaleneacetic acid. White crystals are obtained having a melting point of 97°-100° C.

Analysis for: $C_{18}H_{20}O_3$
Calculated: C, 76.03; H, 7.09.
Found: C, 7 6.3 8; H, 7. 1 0.

EXAMPLE 15

α-Methyl-6-(3.3-dichloroallyloxy)-2-naphthaleneacetic acid

The title compound is prepared according to the method of Example 7 using 3,3-dichloroallyl chloride and racemic 6-hydroxy-(α-methyl-2-naphthaleneacetic acid. White crystals are obtained having a melting point of 107°-109° C.

Analysis for: $C_{16}H_{14}O_3Cl_2$
Calculated: C, 59.10; H, 4.34.
Found: C, 59.43; H, 4.50.

EXAMPLE 16

S-(+)-(α-Methyl-6-(2-quinolinylmethoxy)-2-naphthaleneacetic acid, sodium salt

To a solution of 0.1 N sodium hydroxide (14 mmol) is added the acid of Example 7 (5.0 g, 14 mmol). After 35 minutes, the solid is filtered and dried in vacuo to afford 5.3 g (99%) of white crystals, m.p. 241°-243° C.

Analysis for: $C_{23}H_{18}NO_3Na \cdot 0.9\ H_2O$
Calculated: C, 69.83; H, 5.04; N, 3.54.
Found: C, 69.98; H, 4.78; N, 3.46.

EXAMPLE 17

S-(+)-α-Methyl-6-(2-quinolinylmethoxy)-2-naphthaleneacetic acid, tromethamine salt To a solution of the acid of Example 7 (25.0 g, 69.9 mmol) in 1200 ml refluxing ethanol is added a solution of tris(hydroxymethyl)aminomethane (8.47 g, 69.9 mmol) in 37 ml of water. After 105 minutes, the ethanol is removed in vacuo and ethyl ether is added. The resulting precipitate (31.0 g, 92%) is filtered and dried in vacuo. Recrystallization from ethanol affords white crystals, m.p. 169°-17 1 ° C.

Analysis for: $C_{27}H_{30}N_2O_6$
Calculated: C, 67.77; H, 6.32; N, 5.85.
Found: C, 68.06; H, 6.30; N, 5.82.

EXAMPLE 18

α-Methyl-6-[(7-chloro-2-quinolinyl)methoxyl-2-naphthaleneacetic acid

The title compound is prepared according to the method of Example 7 using 2-bromomethyl-7-chloroquinoline. A crystalline solid is obtained having a melting point of 188°-190° C.

Analysis for: $C_{23}H_{18}ClNO_3$
Calculated: C, 70.50; H, 4.63; N, 3.57.
Found: C, 70.85; H, 4.57; N, 3.46.

EXAMPLE 19

α-Methyl-5-bromo-6-(2-quinolinylmethoxy)-2-naphthaleneacetic acid

The title compound is prepared according to the method of Example 7 using 5-bromo-6-hydroxy-2-naphthaleneacetic acid. White crystals are obtained, m.p. 210°-212° C.

Analysis for: $C_{23}H_8BrNO_3$
Calculated: C, 63.32; H, 4.16; N, 3.21.
Found: C, 63.02; H, 4.06; N, 3.24.

EXAMPLE 20

α-Methyl-6-[(3-phenyl-2-propenyl)oxyl-2-naphthaleneacetic acid

The title compound is prepared according to the method of Example 7 using cinnamyl bromide. A crystalline solid is obtained having a melting point of 175°-177—C.

Analysis for: $C_{22}H_{20}O_3$
Calculated: C, 79.50; H, 6.07.
Found: C, 79.42; H, 6.06.

EXAMPLE 21

6-(2-Quinolinylmethoxy)-2-naphthaleneacetic Acid

A mixture of 2-acetyl-6-methoxynaphthalene* (63.4 g, 0.31 mol), sulfur (16.0, 0.5 g Atoms) and morpholine (55.0 g, 0.63 mol) is heated at 140° C. for 18 hours. After removal of the excess morpholine, concentrated hydrochloric acid (220 ml) and acetic acid (125 ml) are added to the reaction mixture, which is then refluxed for 24 hours. The solvent is removed and 0.5L of water is added. The resulting precipitate is filtered off and added to a hot solution of 60.0 g sodium carbonate in 0.5L of water. This solution is acidified and washed with diethylether. The ether layer is filtered and evaporated to afford 39.0 g (61%) of 6-hydroxy-2-naphthaleneacetic acid as white crystals, m.p. 208°-210° C. The title compound is prepared according to the method of Example 1 using the acid from this example. A pale yellow crystalline solid is obtained having a melting point of 199°-202° C.

* Prepared according to the procedure described in Organic Syntheses VI, 34 (1988).

Analysis for: $C_{22}H_{17}NO_3$
Calculated: C, 76.95; H, 4.99; N, 4.07.
Found: C, 76.60; H, 5.10; N, 3.98.

EXAMPLE 22

α,α-Dimethyl-6-(2-quinolinylmethoxy)-2-naphthaleneacetic acid

To a solution of (α-methyl-6-methoxy-2-naphthaleneacetic acid methyl ester (12.2 g, 50 mmol) in tetrahydrofuran (100 ml) at −70° C. is added a solution of lithium diisopropylamide in cyclohexane (50 ml, 1.5 equiv). After 20 minutes, methyl iodide (4.0 ml, 1.3 equiv) is added followed by hexamethylphosphoraniide (20 ml). After allowing the reaction mixture to warm to room temperature and stir 16 hours, the reaction is quenched by addition of acetic acid (4.3 ml, 75 mmol). The solvent is then removed and the residue is partitioned between ethyl acetate and water. The organic layer is washed with water 3 times and finally with brine. After drying over magnesium sulfate, the organic extract is evaporated to afford a crude solid. Recrystallization of this solid from hexane affords 8.56 g (66%) of α,α-dimethyl-6-methoxy-2-naphthaleneacetic acid methyl ester as white crystals, m.p. 97°-98° C. A solution of this ester (7.4 g, 28.6 mmol) in 48% HBr (50 ml) and acetic acid (50 ml) is refluxed for 3 hours. After the reaction mixture is cooled to room temperature, 0.8 L of water is added and the reaction mixture is extracted with ethyl acetate 5 times. The combined organic extract is washed sequentially with saturated sodium bicarbonate solution and water. After drying over magnesium sulfate, the organic extract is evaporated to afford 6.1 g (93%) of α,α-dimethyl-6-hydroxy-2-naphthaleneacetic acid as white crystals, m.p. 208°-210° C. The title compound is prepared according to the method of Example 7 using α,α-dimethyl-6-hydroxy-2-naphthaleneacetic acid. A white solid is obtained having a melting point of 207°-209° C.

Analysis for: $C_{24}H_{21}NO_3$
Calculated: C, 77.61; H, 5.70; N, 3.77.
Found: C, 77.31; H, 5.69; N, 3.79.

EXAMPLE 23

N-Hydroxy-α-N-dimethyl-6-(2-quinolinylmethoxy)-2-naphthaleneacetamide dehydrate

To a solution of the acid of Example 1 (5.0 g, 13.99 mmole) and dimethylformamide (1.08 ml, 13.99 mmole) in methylene chloride (150 ml) at 0° C. is added oxalyl chloride (3.99 g, 31.47 mmole). After one hour, the mixture is added to another flask containing N-methylhydroxylamine hydrochloride (4.67 g, 55.96 mmole), tetrahydrofuran (50 ml), water (10 ml), and triethylamine (8.49 g, 83.93 mmole). After stirring for 1.5 hours, the reaction mixture is poured into 2N hydrochloric acid. A solid forms, is removed and recrystallized from ethanol, yielding 1.0 g. Further recrystallization from ethanol gives 0.48 g (8.8%), m.p. 170°-172° C.

Analysis for: $C_{24}H_{22}N_2O_3 \cdot 2 H_2O$
Calculated: C, 68.17; H, 5.68; N, 6.62.
Found: C, 67.65; H, 5.21; N, 6.32.

EXAMPLE 24

(S)-N-Hydroxy-α-N-dimethyl-6-(2-quinolinylmethoxy)-2-naphthaleneacetamide

To a solution of the acid of Example 7 (4.5 g, 12.59 mmole) and dimethylformamide (0.97 ml, 12.59 mmol) in methylene chloride (135 ml) at 0° C. is added oxalyl chloride (2.46 ml, 28.32 mmole). After 1 hour, the mixture is added to another flask containing N-methylhydroxylamine hydrochloride (3.4g, 40.70 mmol), tetrahydrofuran (45 ml), water (9 ml) and triethylamine (9.1 ml, 65.5 mmol). After stirring for 1.5 hours, the reaction mixture is poured into 2N hydrochloric acid. A solid forms, is removed and recrystallized from ethanol, yielding 2.2 g. The product is adhered to silica gel (15g) and flash chromatographed using ethyl acetate(7): hexane(3) as eluant. 700 mg (14%) of product is recovered, mp 130°-132° C.

Analysis for: $C_{24}H_{22}N_2O_3$
Calculated: C, 74.00; H, 5.78; N, 7.25.
Found: C, 73.60; H, 5.60; N, 7.10.

EXAMPLE 25

α-Methyl-N-[(4-methylphenyl)sulfonyl]-6-(2-quinolinylmethoxl)-2-naphthaleneacetamide To a solution of the acid of Example 1 (1.0 g, 2.79 mmol), p-toluenesulfonamide (0.47 g, 2.79 mmol) and benzotriazol-1-yloxytris(dimethylamino)phosphonium hexafluorophosphate (1.23 g, 2.79 mmol) in methylene chloride (25 ml) is added triethylamine (0.78 ml, 2 equiv). After stirring overnight, the reaction is quenched by addition of brine. It is then sequentially washed with water, 0.5N hydrochloric acid, and finally water. After drying over magnesium sulfate, the solvent is removed to afford a crude solid. Recrystallization of this solid from ethyl acetate gave 0.55 g (39%) of white crystals, m.p. 201°-205° C.

Analysis for: $C_{30}H_{26}N_2O_4S$
Calculated: C, 70.56; H, 5.13; N, 5.48.
Found: C, 70.58; H, 5.30; N, 5.51.

EXAMPLE 26

(S)-β-methyl-6-(2-quinolinylmethoxl)-2-naphthaleneethanol

To a solution of the acid from Example 7 (3.57 g, 10.0 mmol) in tetrahydrofuran (100 ml) at 0° C. is added lithium aluminum hydride ( 10.0 mmol) as a tetrahydrofuran solution. After 5 days the reaction is quenched by sequential addition of 0.38 ml water, 0.38 ml 15% sodium hydroxide and 1.14 ml water. The solution is filtered, dried over magnesium sulfate and evaporated to 3.0 g (88%) of crude product. Recrystallization of this crude solid from hexane/toluene affords yellow crystals of the title compound, m.p. 129°-13 1 ° C.

Analysis for: $C_{23}H_{21}NO_2$
Calculated: C, 80.44; H, 6.16; N, 4.08.
Found: C, 80.77; H, 6.31; N, 3.85.
$[α]_D = -10.1$ (methanol)

EXAMPLE 27

(S)-α-methyl-6-(2-quinolinylmethoxy)-2-naphthaleneacetal

To a solution of oxalyl chloride ( 0.22 ml, 2.5 mmol) in methylene chloride (10 ml) at −70° C. is added dimethylsulfoxide (0.35 ml, 5.0 mmol). After 2 minutes, the alcohol of Example 26 (0.78 g, 2.27 mmol) in methylene chloride is added. After 15 minutes, triethylamine (1.6 ml, 11.0 mmol) in methylene chloride is added and the reaction is allowed to warm to room temperature. After 3 days, the reaction mixture is added to water (50 ml) and methylene chloride (50 ml). The organic layer is separated and sequentially washed with 1% hydrochloric acid, water, sodium bicarbonate solution, water and finally brine. After drying over magnesium sulfate, the organic extract is evaporated to afford 0.77 g (100%) of crude product. Flash chromatography of this material, eluting with methylene chloride-acetone, followed by recrystallization from toluene-hexane affords white crystals, m.p. 113°–115° C.

Analysis for: $C_{23}H_{19}NO_2$
Calculated: C, 80.92; H, 5.61; N, 4.10.
Found: C, 80.77; H, 5.73; N, 4.41.

EXAMPLE 28

α-Methyl-6-(2-quinolinylmethoxl)-2-naphthaleneacetic acid methyl ester

To a solution of the acid of Example 1 (4.0 g, 11.2 mmol) in tetrahydrofuran (50 ml) is added ethereal diazomethane until the yellow color persists. After addition of acetic acid to the point that the yellow color is quenched, the solvent is evaporated to afford a crude solid. Recrystallization of this solid with ethyl acetate/hexane gives 3.5 g (84%) of a crystalline solid having a melting point of 91°–93° C.

Analysis for: $C_{24}H_{21}NO_3$
Calculated: C, 77.61; H, 5.70; N, 3.77.
Found: C, 77.39; H, 5.81; N, 3.52.

EXAMPLE 29

(S)-α-methyl-6-(2-quinolinylmethoxy)-2-naphthaleneactic acid methyl ester

The title compound is prepared according to the method of Example 28 using the acid from Example 7. A crystalline solid is obtained having a melting point of 96°–98° C.

Analysis for: $C_{24}H_{21}NO_3$
Calculated: C, 77.61; H, 5.70; N, 3.77.
Found: C, 77.25; H, 5.54; N, 3.68.
$[\alpha]_D = +53.8$ (c=0.84, pyridine)

EXAMPLE 30

N-methoxy-α-methyl-6-(2-quinolinylmethoxy)-2-naphthaleneacetamide

To a mixture of the acid of Example 1 (2.32 g, 6.5 mmol), 0-methylhydroxylamine hydrochloride (0.54 g, 6.5 mmol) and 1-ethyl-3-[3-(dimethylamino)propyl]carbodiimide (1.25 g, 6.5 mmol) in tetrahydrofuran (100 ml) is added triethylamine (2.0 ml, 2 equiv). After overnight stirring at room temperature, the solvent is removed and methylene chloride is added. This is followed by sequential washings with 0.05N hydrochloric acid and water (2x). After drying over magnesium sulfate, the solvent is removed to afford a crude solid which is recrystallized from ethyl acetate to afford a white crystalline solid, 0.6 g(24%), m.p. 162°–164° C.

Analysis for: $C_{24}H_{22}N_2O_3$
Calculated: C, 74.59; H, 5.73; N, 7.24.
Found: C, 74.86; H, 5.47; N, 7.38.

EXAMPLE 31

N-Hydroxy-N'-[1-[(S)-6-(2-quinolinylmethoxy-2-naphthalenylethyl]urea

To a solution of the acid from Example 7 (1.0 g, 2.8 mmol) in benzene (25 ml) is added triethylamine (0.39 ml, 1 equiv) followed by diphenylphosphoryl azide (0.6 ml, 1 equiv). After the reaction mixture is heated for 1 hour at 90° C., a solution of hydroxylamine hydrochloride (0.39g, 2 equiv) in triethylamine (0.78 ml) and water (0.5 ml) is added and the reaction mixture is heated at 90° C. for 24 hours. The reaction mixture is then cooled to room temperature and quenched by addition of aqueous ammonium chloride. The resulting precipitate is filtered, washed with water and acetone, dried and recrystallized fi-om aqueous methanol to afford 0.51 g (46%) of white crystals, m.p. 197°–1980° C.

Analysis for: $C_{23}H_{21}N_3O_3$
Calculated: C, 71.30; H, 5.46; N, 10.85.
Found: C, 71.05; H, 5.72; N, 11.00.
$[\alpha]_D = -46.9$ (c 9.9 pyridine)

EXAMPLE 32

Following the procedures outlined herein, there are prepared the following compounds:

2-[(1-hydroxyureido)methyll-6-(2-quinolinylmethoxy)naphthalene

2-[(α-methyl-1-(1-hydroxyureido)methyl]-6-(2-quinolinylmethoxy)naphthalene

2-[2-(1-hydroxyureido)isopropyl-6-(2-quinolinylmethoxy)naphthalene

2-[(1-hydroxyureido)methyl]-6-(2-benzothiazolylmethoxy)naphthalene

2-[(α-methyl-1-(1-hydroxyureido)methyll-6-(2-benzothiazolylmethoxy)naphthalene

2-[2-(1-hydroxyureido)isopropyl-6-(2-benzothiazolylmethoxy)naphthalene

2-[(1-hydroxyureido)methyl]-6-[(2-phenyl-4-thiazolyl)methoxy]naphthalene

2-[(α-methyl-1-(1-hydroxyureido)methyl]-6-[(2-phenyl-4-thiazolyl)methoxy]-naphthalene 2-[2-(1-hydroxyureido)isopropyl]-6-[(2-phenyl-4-thiazolyl)methoxy]naphthalene α-methyl-6-(α-methyl-2-quinolinylmethoxy)-2-naphthaleneacetic acid α-methyl-6-(2-(quinolin-2-yl)isopropoxy)-2-naphthaleneacetic acid α-methyl-6-(quinolin-2-yl-ethenyl)-2-naphthaleneacetic acid

EXAMPLE 33

N-Hydroxy-N'-[1-methyl-1-(2-quinolinyl-methoxy)-2-naphthalenyl]ethyl]urea

The title compound is prepared according to the method of Example 31 using 1.0 g of the acid from Example 22. Sequential recrystallization of the crude product from ethyl acetate and ethanol affords 0.4 g (37%) of a crystalline solid having a melting point of 155°–157° C.

Analysis for: $C_{24}H_{23}N_3O_3$
Calculated: C, 71.80; H, 5.77; N, 10.47.
Found: C, 71.51; H, 5.79; N, 10.10.

EXAMPLE 34

S-(−)-N-Hydroxy-(α-methyl-N-(l-methylethyl)-6-(2-quinolinylmethoxy)-2-naphthaleneacetamide The title compound is prepared according to the method of Example 24 using N-isopropylhydroxylamine hydrochloride. Flash chromatography of the crude product on silica gel eluting with ethyl acetate/methylene chloride/methanol affords a crystalline solid having a melting point of 174°–176° C.

Analysis for: $C_{26}H_{26}N_2O_3$
Calculated: C, 75.34; H, 6.32; N, 6.76.
Found: C, 75.06; H, 6.32; N, 6.66.
$[\alpha]_D = -34.6$ (c=8.2, pyridine)

EXAMPLE 35

N-Hydroxy-N-methyl-N'-[1-[(S)-6-(2-quinolinylmethoxy)-2-naphthalenyl]ethyl]urea

The title compound is prepared according to the method of Example 31 using N-methylhydroxylamine hydrochloride. Recrystallization of the crude product from ethanol affords a crystalline solid having a melting point of 146–148° C.

Analysis for: $C_{24}H_{23}N_3O_3$
Calculated: C, 71.80; H, 5.77; N, 10.47.
Found: C, 71.63; H, 5.72; N, 10.12.
$[\alpha]_D = -24.9$ (c=9.6, pyridine)

EXAMPLE 36

N-Hydroxy-α,α,N-trimethyl-6-(2-quinolinylmethoxy)-2-naphthaleneacetamide

The title compound is prepared according to the method of Example 24 using the acid from Example 22. Recrystallization of the crude product from ethyl acetate affords the desired product as a crystalline solid having a melting point of 168°–170° C.

Analysis for: $C_{25}H_{24}N_2O_3$
Calculated: C, 74.98; H, 6.04; N, 7.00.
Found: C, 75.24; H, 6.00; N, 6.63.

EXAMPLE 37

N-Hydroxy-N-methyl-6-(2-quinolinylmethoxy)-2-naphthaleneacetamide

The title compound is prepared according to the method of Example 24 using the acid from Example 21 and omitting the dimethylformamide. The crude product is added to ethyl acetate, washed sequentially with saturated sodium bicarbonate and water, dried over magnesium sulfate to give a crude solid. Recrystallization of this solid from acetone affords the desired product as a crystalline solid having a melting point of 145°–146° C.

Analysis for: $C_{23}H_{20}N_2O_3$
Calculated: C, 74.18; H, 5.41; N, 7.52.
Found: C, 74.24; H, 5.15; N, 7.46.

EXAMPLE 38

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. The assay of this Example measures the ability of the compounds of the invention to inhibit the synthesis of 5-BETE by rat glycogen elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the ravaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 μM), A23187, is added together with 0.5 μM [$_{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed precoated thin layer chromatographic plates. The samples are then cochromatographed with authentic reference 5-BETE in the solvent system - hexane:ether:acetic acid (50:50:3). After chromatography, the areas associated with 5-HETE standard are identified by autoradiography, cut out and quantitated by liquid scintillation.

The compounds of the invention and the nonsteroidal anti-inflammatory drug naproxen, when tested in this assay at the level of 10 μM, gave the following results in inhibiting the synthesis of the arachidonic acid lipoxygenase oxidation product 5-HETE.

TABLE 1

| Compound of Example No. | % Inhibition of 5-LO (as 5-HETE) | IC$_{50}$ |
|---|---|---|
| naproxen | −94* | |
| 1 | 100 | |
| 2 | 84 | |
| 3 | 24 | |
| 4 | 82 | |
| 5 | 90 | |
| 6 | 100 | |
| 7 | 100 | |
| 8 | 33** | |
| 9 | 86 | |
| 10 | 81 | |
| 11 | 28 | |
| 12 | 48 | |
| 14 | 81 | |
| 16 | 100 | |
| 17 | 85 | |
| 18 | | 11.4 μM |
| 19 | 82 | |
| 20 | 89 | |
| 21 | 95 | |
| 22 | 87 | |
| 23 | 75 | |
| 24 | 100 | |
| 25 | 100 | |
| 26 | 97 | |
| 27 | 100 | |
| 28 | | 0.43 μM |
| 29 | 91 | |
| 30 | 92 | |

*The negative value denotes a potentiation of 5-HETE synthesis.
**Tested at a level of 0.1 μM.

These results show that the compounds of the invention exhibit very significant activity in inhibiting the enzyme, 5-lipoxygenase.

EXAMPLE 39

The procedure of Example 38 is also employed for the determination of the ability of the compounds of the invention to inhibit the synthesis of the arachidonic acid cyclooxygenase oxidation products $TxB_2$ and $PGE_2$.

In this assay, the procedure of Example 38 is carried out as described. However, in order to determine cyclooxygenase activity, the samples are cochromatographed with authentic reference $TxB_2$ and $PGE_2$ in the solvent system ethyl acetate : formic acid (80: 1) and the upper phase of ethyl acetate : isooctane : acetic acid:water (110:50:20:100). After chromatography, the areas associated with the $TxB_2$ and $PGE_2$ standards are identified by autoradiography, cut out and quantitated by liquid scintillation techniques.

The results are calculated as in Example 38.

When tested in this assay the compounds of the invention and the nonsteroidal anti-inflammatory drug naproxen, a well-established inhibitor of cyclooxygenase, at a level of 10 $\mu M$, gave the following results in inhibiting the synthesis of the arachidonic acid cyclooxygenase oxidation products $TxB_2$ and $PGE_2$.

TABLE 2

| Compound of Example No. | % Inhibition of CO (as $TxB_2$) | $IC_{50}$ | % Inhibition of CO (as $PGE_2$) | $IC_{50}$ |
|---|---|---|---|---|
| naproxen | | | 85 | |
| 1 | 28 | | −37* | |
| 2 | 6 | | −26* | |
| 3 | 15 | | −29* | |
| 4 | 12 | | 18 | |
| 5 | | | −35* | |
| 6 | | | −15* | |
| 7 | | | −17* | |
| 8 | | | −7*, ** | |
| 9 | | | −11* | |
| 10 | | | −5* | |
| 11 | | | −3* | |
| 12 | | | −13* | |
| 14 | | | −15* | |
| 16 | | | −13* | |
| 17 | | | 20 | |
| 18 | | | | >50 $\mu M$ |
| 19 | | | −21* | |
| 20 | | | 14 | |
| 21 | | | | >250 $\mu M$ |
| 22 | | | −28* | |
| 23 | | | 17 | |
| 24 | | | 13 | |
| 25 | | | −103* | |
| 26 | | | 5 | |
| 27 | | | −62* | |
| 28 | | | | >10 $\mu M$ |
| 29 | | | −17* | |
| 30 | | | −27* | |

*The negative values denotes a potentiation of $PGE_2$ synthesis.
**Tested at level of 0.1 $\mu M$.

These results show that the compounds of the invention, in contradistinction to naproxen, are virtually devoid of cyclooxygenase inhibitory activity, having activity substantially only on the lipoxygenase pathway of arachidonic acid oxidation.

EXAMPLE 40

The assay of this Example measures the in vivo ability of the compounds of the invention to inhibit the bronchospasm induced in guinea pigs by the exogenously administered leukotrienes $C_4$ and/or $D_4$.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes. The animals are then pretreated with succinylcholine (2 mg/kg i.v.) and indomethacin (10 mg/kg i.v.) in trizma 8.3 buffer, 9 minutes prior to leukotriene challenge. Submaximal bronchoconstrictor responses are established in control animals by varying the dose-levels of leukotriene. Intravenous dose-levels for $LTC_4$ range from 0.4 to 0.6 $\mu g/kg$ and for $LTD_4$ the range is from 0.3 to 0.5 $\mu g/kg$. The aerosol bronchoprovocation dose for $LTC_4$ is generated from 1.6 $\mu M$ solution and for $LTD_4$ from a 2.0 $\mu M$ solution.

Test drugs (dissolved in a solvent such as propylene glycol, polyethylene glycol 400 or saline) are administered either intraduodenally, by aerosol or intragastrically at 2 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\% \text{ max AUC} = \frac{3(1 \text{ min}) + 4(3 \text{ min}) + 2(5 \text{ min})}{10(\text{max})} \times 100 \quad (1$$

Drug effects are reproted as percent inhibition of % max AUC values obtained from appropriate control animals (equation 2):

$$\% \text{ inhibition} = \frac{\% \text{ max AUC control} - \% \text{ max AUC treated}}{\% \text{ max AUC control}} \times 100 \quad (2$$

Student's t-test for unpaired data is used to determine statistical significance (p<0.05). $IC_{50}$ values can also be determined by inverse prediction from linear regression lines through points between 10% and 90% inhibition.

The results for compounds of the invention are as follows:

TABLE 3

| Compound administered at 10 minutes before induction of bronchospasm using $LTD_4$ | | |
|---|---|---|
| Compound of Example Number | Dose* mg/kg | % Inhibition |
| 1 | 25 | 75 |
| 2 | 25 | −76 |

TABLE 3-continued

Compound administered at 10 minutes before
induction of bronchospasm using LTD$_4$

| Compound of Example Number | Dose* mg/kg | % Inhibition |
| --- | --- | --- |
| 3 | 25 | 80 |
| 4 | 25 | 52 |

* = intraduodenally administered

The results show that compounds of the invention have significant in vivo activity against LTD$_4$ induced bronchoconstriction.

EXAMPLE 41

The compounds of the invention are tested to measure their in vivo ability to inhibit the bronchoconstriction induced in anesthetized guinea pigs by exogenously administered antigen.

This assay is carried out as follows:

Male Hardey guinea pigs (400-700 gm) are sensitized three weeks prior to antigen (ovalbumin-OA) challenge as follows: each guinea pig is given two intramuscular injections—0.35 ml of Grade V OA, 50 mg/ml, into each hindlimb.

Guinea pigs, fasted overnight but allowed water ad-libitum, are anesthetized with 1.2 g/kg of urethane (intraperitoneal). Supplemental doses of 0.6 g/ml of urethane are administered intraperitoneally as needed. One carotid artery and one jugular vein are cannulated to allow for the monitoring of blood pressure and the administration of drugs, respectively. A duodenal cannula is inserted for intraduodenal dosing studies. The trachea of each animal is cannulated and connected to a Harvard respirator. Spontaneous respiration is abolished with succinylcholine (2.5 mg/kg, intravenous and 1.0 ml of a 0.5 mg/ml solution, intraperitoneal). Animals are ventilated at the rate of 65 breaths per minute and an overflow pressure of approximately 8 cm water is maintained as the baseline pressure. Respiratory overflow pressure is measured from a side arm off the tracheal cannula which is connected via a Gould or Beckman pressure transducer to a suitable strip chart recorder. Each animal is allowed a 20-30 minute stabilization period.

After stabilization, each animal is given, intravenously, 2.5 mg/kg pyrilamine (mepyramine), 0.1 mg/kg propranolol and 10.0 mg/kg indomethacin, at 20, 15 and 10 minutes, respectively, prior to 10.0 mg/kg OA challenge. Pyrilamine is a histamine (H$_1$) receptor antagonist which is used to block the effects of any histamine released upon OA challenge. Propranolol, a $\beta$-antagonist, is administered to block reflex bronchodilation mechanisms. Indomethacin, a cyclooxygenase inhibitor, is given to inhibit the production of products of the cyclooxygenase pathway. The above treatment results in a leukotriene-dependent bronchoconstriction upon OA challenge.

Test compounds are administered intravenously, perorally, or intraduodenally at appropriate times prior to OA challenge. Only one broncho-constriction per animal is induced. For intravenous administration, drugs are dissolved in saline, or saline containing dilute NAOH, HCl or dimethyl sulfoxide according to their solubility. Control experiments are used to determine the effects of solvents on the measured parameters, and test data is corrected for any significant solvent effects. At the end of the experiment, each animal is euthanized with an injection of approximately 10 ml of air through the jugular vein cannula.

Bronchoconstriction is assessed as increases in respiratory overflow pressure (cm H$_2$O). Changes in blood pressure (mm Hg) are also recorded.

Test compound-induced changes in the respiratory overflow pressure are assessed as percent changes from control experiments. Since only one bronchoconstriction is induced per animal, a set of control and drug treated animals are run concurrently. At least 5 animals are used in each treatment group. The net change in overflow pressure is measured 5 minutes after antigen challenge and is calculated as follows. The baseline overflow pressure is subtracted from the overflow pressure 5 minutes after OA challenge for each specific animal. The net increase in overflow pressures for a specific group is then meaned and the standard error is derived for that group as well as for the control group. Mean test compound changes in the respiratory overflow pressure may be compared to the mean control overflow pressure using paired "t" test. Additional analysis of variance may be performed between groups of animals administered different regimens of test compounds. The percent change value for the drug treated group versus the control group is calculated as follows:

$$\% \text{ INHIBITION} = [(OP2 - OP1)/OP2] \times 100$$

Where OP1 is the net increase in overflow pressure for the drug treated group. OP2 is the net increase in overflow pressure for its paired control group.

When tested in this assay, the compounds of the invention gave the following results:

TABLE 4

Compounds Orally Administered 4 Hours Before
Induction of Bronchoconstriction

| Compound of Example No. | ED$_{50}$ (mg/kg) |
| --- | --- |
| 7 | 100 |
| 16 | 15 |
| 17 | 7 |

The results show that compounds of the invention, especially certain salts, possess extremely significant activity against ovalbumin-induced bronchoconstriction.

EXAMPLE 42

The compounds of the invention are further tested in the rat carrageenan paw edema assay to determine their ability to inhibit the acute inflammatory response.

This assay is carried out as follows.

140-180 gm male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine line statistical significance.

The activity of standard drugs in this assay is as follows:

| Drug | Oral ED$_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, the compounds of the invention gave the following results:

TABLE 5

| Compound of Example No. | % Inhibition of 50 mg/kg (peroral) |
|---|---|
| 1 | 42 |
| 2 | 24 |
| 3 | 32 |
| 4 | 30 |

The results show that the compounds tested have activity in the rat carrageenan paw edema assay, evidencing an effect on the acute inflammatory response.

EXAMPLE 43

The compounds of the invention are further tested in the reverse passive Arthus pleurisy assay to evaluate their effectiveness in inflammatory mediator release and/or the fluid and cellular phases of an inflammatory response.

This assay is carried out as follows:

A reverse passive Arthus reaction is induced in the pleural cavity of male Lewis rats (150–200 g; fasted overnight prior to use) by the intravenous administration of bovine serum albumin (BSA; 4 mg/0.2 ml) followed 30 minutes later by the injection of rabbit anti-BSA (1 mg/0.2 ml; lyophilized IgG fraction; Organon Teknika, West Chester, Pa.) into the right pleural space under halothane anesthesia. Drugs or vehicle (0.5% Tween-80) control are administered orally in a volume of 1 ml/100 g body weight at 1 hour prior to the anti-BSA. Animals are sacrificed at either the time of peak eicosanoid production (i.e. 5 minutes after anti-BSA for immunoreactive TxB$_2$, 10 minutes for immunoreactive LTC$_4$, 20 minutes for immunoreactive LTC$_4$) or at the time of peak neutrophil infiltration (4 hours after anti-BSA) by CO$_2$ inhalation. The pleural cavity is then exposed, the fluid exudate removed by gentle vacuum aspiration and the volume of exudate is recorded. For the determination of cellular infiltration, the pleural cavity is rinsed with 3 ml of 0.1 % EDTA in sterile saline, and the recovered wash is pooled with the exudate. Cell number is determined on a model ZBI Coulter counter. For determination of eicosanoid production, undiluted pleural exudate is microfuged and the supernatant is extracted with ethanol (8–10 times volume). Extracts are either stored at −20° C., or are evaporated to dryness under a stream of N$_2$ and reconstituted in radioimmunoassay (RIA) buffer.

Eicosanoids are quantitated by RIA according to the procedure specified by the RIA kit manufacturer (Advanced Magnetics, Cambridge, Mass.). Briefly, 100 μl of 3H-labeled eicosanoid and 100 μl of specific antibody are sequentially added to 100 μl of extracted pleural exudate in BGG-phosphate buffer which contains 0.01 M phosphate, 0.1% bovine gamma globulin and 0.1% sodium azide at pH 7.0. Antibody-bound eicosanoid is separated from unbound eicosanoid by the addition of 750 μl of dextran (0.4%)-coated charcoal (0.4% Norit A) containing 0.1% sodium azide. The mixture is centrifuged at 2000 RPM at 5° C. for 15 minutes to pellet the charcoal and adsorbed unbound eicosanoid. Antibody-bound labeled eicosanoid is quantitated by counting in a liquid scintillation counter, and is correlated to concentration by a standard curve.

Inflammatory cells are expressed as 10$^6$ cells/ml, pleural exudate is expressed as ml of fluid, and the amount of eicosanoids in the pleural cavity is expressed as ng/ml of exudate. Mean ±S.E.M. is determined for each group. Percent inhibition (% I) of cell number, exudate volume and eicosanoid production is calculated for vehicle-treated control groups, and the responses in drug-treated rats are then expressed as the mean % I of control. The ED$_{30}$ or ED$_{50}$ with 95% confidence limits is calculated by the method of Litchfield and Wilcoxon, J. Pharmac. Exp. Ther., 96, 99–113 (1949).

The activity of standard drugs in this assay is as follows:

| A. Inflammatory Mediator Release: | | | |
|---|---|---|---|
| Antiinflammatory Drug | Class | ED$_{50}$ (mg/kg p.o.) TxB$_2$ | LTB$_4$ |
| Indomethacin | NSAID; CO inhibitor | 0.16 | 12% Inh (4 mg/kg) |
| Naproxen | | 0.24 | 0% Inh (4 mg/kg) |
| Diclofenac | | 6.0 | 0% Inh (10 mg/kg) |
| Ketoprofen | | 0.18 | 35% Inh (10 mg/kg) |
| Wy-50,295-A | LO-Inhibitor | 0% Inh (75 mg/kg) | 15 |
| BW540C | Mixed CO/LO inhibitor | 19 | 30 |
| BW755C | | 18 | 23 |
| Phenidone | | 69 | 10 |
| B. Pleural Inflammation: | | | |
| Antiinflammatory Drug | Class | ED$_{30}$ (mg/kg p.o.) Fluid Exudation | Cellular Influx |
| Indomethacin | NSAID; CO Inhibitor | 2.5 | 19% Inh (8 mg/kg) |
| Naproxen | | 3.9 | 29% Inh (8 mg/kg) |
| Piroxican | | 1.0 | 3.0 |
| BW755C | Mixed CO/LO Inhibitor | 14 | 28 |
| Phenidone | | 21 | 23 |
| Dexamethasone | Steroid | 0.05 | 0.13 |

When tested in this assay, the compounds of the invention gave the following results:

TABLE 6

| Compound of Example No. | ED$_{50}$ (mg/kg) |
|---|---|
| 7 | 15 |
| 16 | 3.2 |
| 17 | 1.3 |
| 24 | 5.0 |

The results show that the compounds tested have a very significant effect in inhibiting the release of inflammatory mediators and in inhibiting the fluid and cellular phases of the inflammatory response.

EXAMPLE 44

The compounds of the invention are tested in the rat acute gastroirritation assay to examine their potential for causing gastric irritation when administered at doses exceeding the effective dose. The nonsteroidal anti-inflammatory drug naproxen is tested as a standard of a compound known to possess gastroirritant This assay is carried out as follows:

Male Sprague-Dawley rats (190–220 g) are fasted for 18 hours prior to drug administration. Rats are divided into groups of 8 and coded (i.e., observer of gastric lesions is not aware of drug treatment). Drugs were dissolved or suspended in 0.5% Tween 80 and administered by gastric intubation in a volume of 1 ml/100 g body weight, control rats receiving only Tween 80. Four hours after drug administration, rats are evaluated by recording the incidence and severity of gastroirritation using the following scoring system: 0) No irritation or lesions; 1) irritation (redness); 2)$\leq$5 lesions (ulcers) and 3)>5 lesions. Dunnett's test ($\alpha=0.05$) was used to calculate the mean $\pm$SE of each test group and the statistical significance.

The results of this assay are presented in Table 7.

TABLE 7

| Compound of Example No. | Dose mg/kg | % of rats with GI lesions |
|---|---|---|
| naproxen | 25 | 100 |
| 1 | 300 | 0 |
| 10 | 400 | 0 |
| 11 | 400 | 0 |
| 12 | 400 | 25 |

The results show the compounds of the invention to have little potential for acute gastroirritation when compared to naproxen.

EXAMPLE 45

The assay of Example 44 is also used to measure the cytoprotective activity of the compounds against acute gastroirritation induced by a nonsteroidal anti-inflammatory drug (NSAID).

The assay is carried out as presented in Example 44 with the following modifications: one hour before administration of the NSAID, the rats perorally receive either vehicle (1 ml/100 g body weight of 0.5% Tween 80) or drug (100 mg/kg); at 0 hour the rats perorally receive 25 mg/kg of the NSAID naproxen or vehicle (1 ml/100 g body weight of 0.5% Tween 80); at 4 hours post-dosing the rats are sacrificed and gastroirritation assessed as described in Example 44.

The results are presented in Table 8.

TABLE 8

| Compound of Example No. | Dose mg/kg | % of Rats With Lesions | Comments |
|---|---|---|---|
| vehicle | | 12.5 | — |
| naproxen | 25 | 75.0 | — |
| 7 | 100 | 87.5 | no protection |
| 10 | 100 | 37.5 | protection |
| 11 | 100 | 50.0 | moderate protection |

EXAMPLE 46

The assay of this Example measures the ability of the compounds tested to inhibit 5-lipoxygenase in human whole blood.

This assay is carried out as follows:

Blood is obtained in 50–100 ml quantities from male donors. White blood cell counts and differentials are made. Two ml of blood are placed in a 15 ml polypropylene test tube. Compounds are solubilized in dimethylsulfoxide and diluted 1.10 in 10% bovine serum albumin in phosphate buffered saline, pH 7.4 resulting in a final dimethylsulfoxide concentration of 0.1% in the blood. Then, compounds are added to the blood in a shaking water bath at 37° C. for 10 minutes prior to the addition of 30 $\mu$M calcium ionophore (A23187; Sigma). After ionophore administration, whole blood samples are mixed and incubated for 20 minutes at 37° C. in a shaking water bath. Incubation is terminated by placing samples in an ice bath and immediately adding ethylene glycol-bis-($\beta$-aminoethyl ether)-N,N,N',N'-tetraacetic acid (10 mM). Samples are mixed and centrifuged at 1200$\times$g for 15 minutes at 4° C. Preparation of samples for evaluation by RIA or ELISA is carried out by the following protocol. Plasma is removed from sample tubes, placed in 15 ml polypropylene test tubes containing 8 ml methanol, and then vortexed to precipitate protein. Samples are stored at $-70°$ C. overnight. The next day, samples are centrifuged at 200$\times$g for 15 minutes at 4° C. to pellet the precipitate. Samples are dried in a Savant speed vac concentrator, reconstituted to original volume with ice cold RIA or ELISA buffer, and stored at $-70°$ C. until assayed. The assay for eicosanoids (LTB$_4$, TxB$_2$, and PGE$_2$) is performed as described by the manufacturer of the [$^3$H]-RIA kit or ELISA kit (LTB$_4$-Amersham, TxB$_2$ and PGE$_2$ - Caymen Chemical).

The total eicosanoid level in 2 ml of blood is calculated and reported as ng/10$^6$ neutrophils. Significance is determined by a one-way analysis of variance with least significant difference (LSD) comparisons to control (p$\leq$0.05) and IC$_{50}$'s ($\mu$M) are determined by regression analysis (Finney, 1978). Drug effects are expressed as percent change from control values.

Compounds tested in vitro are solubilized in dimethylsulfoxide and diluted 1:10 in 10% bovine serum albumin in phosphate buffer saline resulting in a final dimethylsulfoxide concentration of 0.1 % in the blood.

The results for compounds of the invention tested in this assay are presented in Table 9.

TABLE 9

| Compound of Example No. | Dose ($\mu$M) | % Inhibition of LTB$_4$ | (IC$_{50}$) |
|---|---|---|---|
| A-64077 | 5 | 72 | |
| L-663,536 | 3 | 96 | |
| 17 | 25 | 19 | |
| 23 | 5 | 45 | (18.7 $\mu$M) |
| 24 | 5 | 44 | (16.2 $\mu$M) |
| 25 | 25 | 45 | |
| 26 | 100 | 8 | |
| 29 | 50 | 24 | |
| 30 | 50 | 13 | |
| 33 | 25 | 54 | |
| 34 | 25 | 48 | |
| 35 | 25 | 48 | (33.9 $\mu$M) |
| 36 | 25 | 14 | |
| 37 | 25 | 85 | (0.5 $\mu$M) |

What is claimed is:

1. A compound having the formula

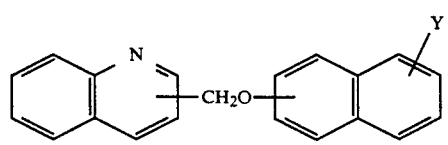

wherein
Y is

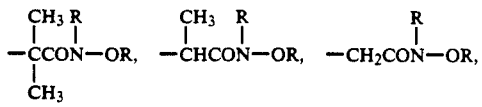

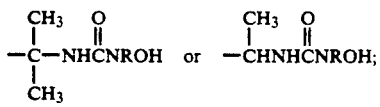

R is hydrogen or lower alkyl;

or a pharmaceutically acceptable salt thereof.

2. The compound of claim 1, having the name N-hydroxy-N'-[1-methyl-1-[6-(2-quinolinylmethoxy)-2-naphthalenyl]ethyl]urea.

3. The compound of claim 1, having the name S-(−)-N-hydroxy-α-methyl-N-(1-methylethyl)-6-(2-quinolinylmethoxy)-2-naphthaleneacetamide.

4. The compound of claim 1, having the name N-hydroxy-N-methyl-N'-[1-[(S)-6-(2-quinolinylmethoxy)-2-naphthalenyl]ethyl]urea.

5. The compound of claim 1, having the name N-hydroxy-α,α,N-trimethyl-6-(2-quinolinylmethoxy)-2-naphthaleneacetamide.

6. The compound of claim 1, having the name N-hydroxy-N-methyl-6-(2-quinolinylmethoxy)-2-naphthaleneacetamide.

* * * * *